United States Patent
Murphy et al.

(10) Patent No.: US 7,271,290 B2
(45) Date of Patent: Sep. 18, 2007

(54) MONOFORMYLATED ARYLAMINE PROCESSES AND COMPOUNDS

(75) Inventors: Leanne Dawn Murphy, Etobicoke (CA); Roger Earl Gaynor, Oakville (CA)

(73) Assignee: Xerox Corporation, Stamford, CT (US)

( * ) Notice: Subject to any disclaimer, the term of this patent is extended or adjusted under 35 U.S.C. 154(b) by 135 days.

(21) Appl. No.: 11/225,963

(22) Filed: Sep. 14, 2005

(65) Prior Publication Data

US 2007/0060775 A1 Mar. 15, 2007

(51) Int. Cl.
*C07C 211/54* (2006.01)
(52) U.S. Cl. ................................. 564/307; 564/433
(58) Field of Classification Search .................. None
See application file for complete search history.

(56) References Cited

U.S. PATENT DOCUMENTS

| | | | |
|---|---|---|---|
| 2,437,370 A | 3/1948 | Wilson | 564/370 |
| 2,558,285 A | 6/1951 | Wilson | 564/433 |
| 3,121,006 A | 2/1964 | Middleton et al. | 430/31 |
| 4,298,697 A | 11/1981 | Baczek et al. | 521/27 |
| 4,338,390 A | 7/1982 | Lu | 430/108.2 |
| 4,560,635 A | 12/1985 | Hoffend | 430/108.2 |
| 6,172,264 B1 | 1/2001 | Kobayashi et al. | 564/433 |
| 6,645,686 B1 | 11/2003 | Fu et al. | 430/58.4 |
| 6,787,277 B2 | 9/2004 | Tong et al. | 430/58.8 |
| 6,824,940 B2 | 11/2004 | Wu et al. | 430/66 |

OTHER PUBLICATIONS

Database CAPLUS on STN, Acc. No. 1997:250102, Anzai et al., JP 09031035 (Feb. 4, 1997) (abstract).*
U.S. Appl. No. 11/116,255, filed Apr. 28, 2005, of Leanne D. Murphy and Roger Earl Gaynor, entitled "Process for preparing a polyformyl arylamine" 24 pages, not yet published.

\* cited by examiner

*Primary Examiner*—Brian Davis
(74) *Attorney, Agent, or Firm*—Marylou J. Lavoie, Esq. LLC

(57) ABSTRACT

A process comprising for example reacting a substituted or unsubstituted arylamine or a mixture thereof with a Vilsmeier reagent in a solvent system comprising acetonitrile as a sole solvent or a solvent system comprising acetonitrile and one or more solvents selected from toluene, xylene, chlorobenzene, dichlorobenzene, dichloromethane, 1,2-dichloroethane, or a combination thereof.

16 Claims, No Drawings

MONOFORMYLATED ARYLAMINE PROCESSES AND COMPOUNDS

TECHNICAL FIELD

The present disclosure relates generally to a process for preparing a monoformylated arylamine.

BACKGROUND

Electrophotographic imaging members, i.e., photoreceptors, typically include a photoconductive layer formed on an electrically conductive substrate. The photoconductive layer is an insulator in the dark so that electric charges are retained on its surface. Upon exposure to light, the charge is dissipated. A latent image is formed on the photoreceptor by first uniformly depositing electric charges over the surface of the photoconductive layer by one of any suitable means known in the art. The photoconductive layer functions as a charge storage capacitor with charge on its free surface and an equal charge of opposite polarity (the counter charge) on the conductive substrate. A light image is then projected onto the photoconductive layer. On those portions of the photoconductive layer that are exposed to light, the electric charge is conducted through the layer reducing the surface charge. The portions of the surface of the photoconductor not exposed to light retain their surface charge. The quantity of electric charge at any particular area of the photoconductive surface is inversely related to the illumination incident thereon, thus forming an electrostatic latent image.

The photo-induced discharge of the photoconductive layer requires that the layer photogenerate conductive charge and transport this charge through the layer thereby neutralizing the charge on the surface. Two types of photoreceptor structures have been employed: multilayer structures wherein separate layers perform the functions of charge generation and charge transport, respectively, reference, for example, U.S. Pat. Nos. 6,824,940 and 6,787,277, the disclosures of each of which are totally incorporated by reference herein; and single layer structures in which photoconductors perform both charge generation and charge transport functions. These layers are formed on an electrically conductive substrate and may include an optional charge blocking layer and an adhesive layer between the conductive substrate and the photoconductive layer or layers. Additionally, the substrate may comprise a non-conducting mechanical support with a conductive surface. Other layers for providing special functions such as incoherent reflection of laser light, dot patterns for pictorial imaging, or subbing layers to provide chemical sealing and/or a smooth coating surface may also be employed. A typical single layer photoreceptor comprises a photogenerating pigment, a thermoplastic binder, a hole transport material, and an electron transport material.

There are many charge transport materials available for electrophotography, reference for example, U.S. Pat. No. 6,645,686, the disclosure of which is hereby totally incorporated by reference herein. Typical charge transport materials include triarylamines.

Charge transporting triarylamines for electrophotographic photoreceptors can be prepared using the Vilsmeier reaction. The Vilsmeier Reaction (or Vilsmeier-Haack Reaction) allows the formylation of electron-rich arenes. The formylating agent, also known as the Vilsmeier Reagent or Vilsmeier-Haack Reagent, is formed in situ from N,N-dimethylformamide (DMF) and phosphorous oxychloride ($POCl_3$).

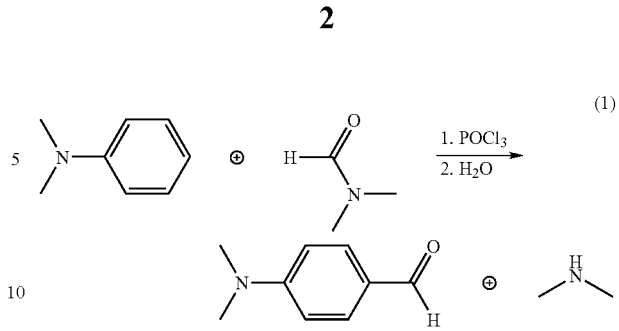

(1)

Reference, for example, U.S. Pat. Nos. 2,558,285 and 2,437,370, the disclosures of each of which are totally incorporated by reference herein.

The traditional Vilsmeier reaction, when used for the monoformylation of triarylamine molecules, requires a large excess of Vilsmeier Reagent (DMF and $POCl_3$) or a solvent system to dissolve the starting material. Solvent free (neat) systems result in extremely viscous reaction mixtures that lead to safety and manufacturing issues. Vilsmeier Reagent is highly corrosive and presents significant safety hazards due to its exothermic nature. Further, use of Vilsmeier Reagent in excess results in high levels of impurities. When a solvent is used in the Vilsmeier Reaction, the viscosity issues are alleviated only if the solvent is miscible with the Vilsmeier Reagent. Most solvents allow multiple formylated products along with other impurities. Many solvents also interfere with hydrolysis and isolation of the end product.

The disclosures of each of the foregoing U.S. patents are each incorporated by reference herein in their entireties. The appropriate components and process aspects of the each of the foregoing U.S. patents may be selected for the present compositions and processes in embodiments thereof.

SUMMARY

Aspects illustrated herein relate to a process comprising reacting an arylamine, for example, a substituted arylamine, an unsubstituted arylamine, or a mixture thereof, with a Vilsmeier reagent and acetonitrile as a sole solvent. Aspects further illustrated include, for example, a process comprising reacting an arylamine with a Vilsmeier reagent and a solvent system comprising acetonitrile and a second solvent selected from an aromatic solvent, an aliphatic solvent, or a combination thereof. In selected embodiments, the second solvent comprises, for example, toluene, xylene, chlorobenzene, dichlorobenzene, dichloromethane, 1,2-dichloroethane, or a combination thereof.

Aspects illustrated herein further relate to a monoformyl arylamine compound prepared by reacting an arylamine, for example a substituted or unsubstituted arylamine, or a mixture thereof with a Vilsmeier reagent in a solvent system comprising acetonitrile as a sole solvent, or, in selected embodiments, a solvent system comprising acetonitrile and further an additional solvent or combination of solvents, for example, a second solvent selected from an aromatic solvent, an aliphatic solvent, or a combination thereof, such as, for example, toluene, xylene, chlorobenzene, dichlorobenzene, dichloromethane, 1,2-dichloroethane, or a combination thereof.

Aspects illustrated herein further relate to a photoconductive imaging member comprising a charge transport layer comprising a charge transport material formed from a monoformyl arylamine, wherein the monoformyl arylamine is prepared by reacting a substituted or unsubstituted arylamine or a mixture thereof with a Vilsmeier reagent in the presence of a solvent system comprising acetonitrile as a sole solvent or a solvent system comprising acetonitrile and one or more solvents selected from the group consisting of toluene, xylene, chlorobenzene, dichlorobenzene, dichloromethane, 1,2-dichloroethane, or a combination thereof.

The present process provides many of the advantages illustrated herein. For example, the process provides a solvent system which reduces the need for high excesses of Vilsmeier Reagent and provides a cleaner or purer product than previously available. It is shown that the use of acetonitrile in the Vilsmeier Reaction allows rapid monoformylation of a triarylamine without overreaction byproducts from multiple formylations. The presence of a solvent overcomes and alleviates the problems associated with the viscous reaction mixture, providing safer manufacturing practices and reduced excesses of Vilsmeier Reagent. Acetonitrile can also be used in combination with a cosolvent, for example, an aromatic solvent or an aliphatic solvent, for example, 1,2-dichloroethane, toluene, which dissolves the starting material at a lower temperature, therefore allowing the reaction to occur at a lower temperature.

These and other features and advantages will be more fully understood from the following description of certain specific embodiments taken together with the accompanying claims.

DESCRIPTION

The Vilsmeier Reaction is the method used for the formylation of intermediates in the manufacture of the triarylamine class of charge transport small molecules. In these reactions, triarylamines are reacted with Vilsmeier reagent. Monoformylation occurs rapidly and is followed closely by the onset of bisformylation. The product is generally a mixture of monoformylated and bisformylated material which can involve complex purification steps (for example, column chromatography). The amount of each depends on the reaction conditions (for example, time, temperature). The solvent system is one factor which greatly influences the conversion from monoformylated to bisformylated product.

In some cases the reaction is performed neat (without solvent). This requires high excesses of the Vilsmeier Reagent in order to properly dissolve the starting material. Solvents are often added to reduce viscosity, resulting in a mixture with easier handling capabilities. The problem with most solvents, however, is that they typically accelerate the onset of bisformylation while inhibiting complete conversion. As well, most solvents contribute to the formation of other impurities and can interfere with hydrolysis and isolation of the end product.

The present disclosure relates to a process for preparing a monoformyl arylamine comprising reacting a substituted or unsubstituted arylamine or a mixture thereof with a Vilsmeier reagent in the presence of acetonitrile. The Vilsmeier reagent can be prepared from an N-substituted formamide and a halogenating agent.

In an embodiment, the Vilsmeier reagent can be used in a Vilsmeier-Haack reaction. A "Vilsmeier-Haack reaction" is understood to mean the formylation of activated aromatic or heterocyclic compounds with a N-substituted formamide and a halogenating agent Non-limiting examples of an N-substituted formamide for use as a formylating agent include N,N-dimethylformamide, N-methylformanilide, N-formylmorpholine, and N,N-diisopropylformamide, or a combination thereof. In an embodiment, the N-substituted formamide can be N,N-dimethylformamide and N-methylformanilide.

Non-limiting examples of the halogenating agent which can react with the N-substituted formamide to produce a Vilsmeier reagent include phosphorus oxychloride, pyrophosphoryl chloride, phosgene, oxalyl chloride, thionyl chloride, triphenylphosphine-bromine complex, and hexachlorotriphosphor triene, or a combination thereof. In an embodiment, the halogenating reagent can be selected from phosphorus oxychloride, pyrophosphoryl chloride, phosgene, and thionyl chloride.

The reaction can be carried out by a process which can comprise adding to a reaction vessel from about 1 to about 5 molar equivalents of an N-substituted formamide with the halogenating agent being equivalent, although not limited. The halogenating reagent can be added dropwise to the reaction vessel to prepare a Vilsmeier reagent in situ. In addition, the reaction mixture can comprise any desired or effective amount of acetonitrile. The amount of acetonitrile used in the disclosed process can vary and can be readily determined by one of ordinary skill in the art. About 1 equivalent of a substituted or unsubstituted arylamine can be added to the reaction vessel.

Alternately, pre-prepared Vilsmeier reagent can be added in a selected quantity to the monoformylation reaction vessel.

It is believed, without being limited to any particular theory, that the use of acetonitrile as a solvent enables lesser amounts of the Vilsmeier reagent to be selected for completion of the reaction process. In a comparison amongst several solvents, acetonitrile was the only solvent which inhibited multiple formylations. Acetonitrile was found to have this effect even when provided in combination with other solvents. The use of acetonitrile provides the effect of reducing the amount of Vilsmeier Reagent required for the reaction. For example, about 3, and as a further example, about 2.0, and as a further example, about 1.1 molar equivalents of a Vilsmeier reagent can be selected for the present process employing a solvent system comprising acetonitrile alone or acetronitrile in combination with one or more co-solvents.

Suitable aromatic or aliphatic co-solvents can be selected to help dissolve the starting materials. For example, suitable co-solvents for use in combination with acetonitrile include, but are not limited to, for example, toluene, xylene, chlorobenzene, dichlorobenzene, dichloromethane, 1,2-dichloroethane, or a combination thereof.

It has been shown that use of acetonitrile as an exclusive solvent results in a product that is easily isolated in high yields and requires little or no further purification.

The substituted or unsubstituted arylamine or a mixture thereof for use in the disclosed process can be represented by the following formula (I):

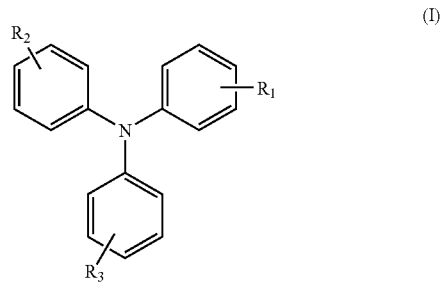

(I)

wherein $R_1$, $R_2$, and $R_3$, can independently be the same or different, and can represent a hydrogen atom, an alkyl group, an alkoxy group, a phenoxy group, a halogen atom such as fluoride, chloride, or bromide, or an aryl group or substituted aryl group. The lower alkyl group can have from about 1 to about 15 carbon atoms, for example from about 2 to about For example, the present process can comprise the monoformylation of a triarylamine in the presence of Vilsmeier Reagent comprising N,N-dimethylformamide and phosphorous oxychloride and acetonitrile solvent to provide a monoformylated triarylamine reaction product represented as follows.

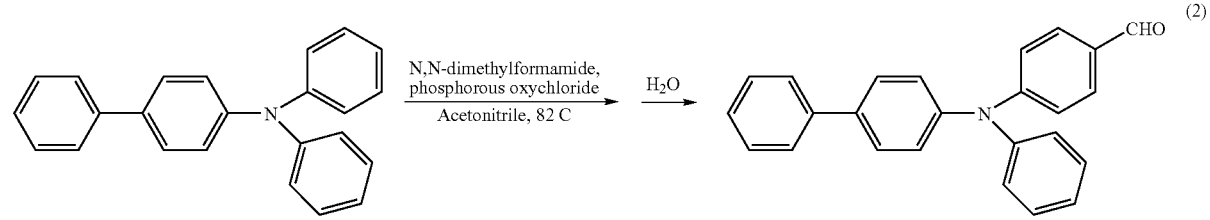

10 carbon atoms. In an embodiment, the lower alkyl group can be selected from the group consisting of methyl, ethyl, propyl, butyl, pentyl, and hexyl groups. The aryl or substituted aryl group can comprise from about 6 to about 30 carbon atoms, and for example from about 6 to about 20 carbon atoms, such as phenyl, naphthyl, phenaphthyl, biphenyl, and the like. Illustrative examples of substituted aryl groups are methylphenyl, ethylphenyl, propylphenyl, butylphenyl, dimethylphenyl, trimethylphenyl, tetramethylphenyl and the like.

The substituted or unsubstituted arylamine or a mixture thereof can have limited solubility in liquids at ambient temperature. For example, the substituted or unsubstituted arylamine can solubilize appreciably at temperatures greater than about 50° C., for example greater than about 90° C., and as a further example greater than about 110° C.

The reaction temperature is limited by the boiling point of the solvent system selected. The boiling point of acetonitrile is 81.6° C.; therefore, the reaction would not be run above this temperature with an acetotonitrile solvent system. The reaction can be effected at temperatures from about room temperature (about 23° C.) to about 150° C., from about room temperature to about 90° C., from about 70° C. to about 85° C., from about 80° to about 85°, or above about 70° C., although not limited except with respect to the solvent as noted. The conversion of the substituted or unsubstituted arylamine or a mixture thereof to the monoformyl arylamine proceeds to completion within a reaction time of up to about 3 hours, for example less than about 1 hour.

The monoformyl arylamine prepared by the process disclosed herein can be represented by the following formula (II):

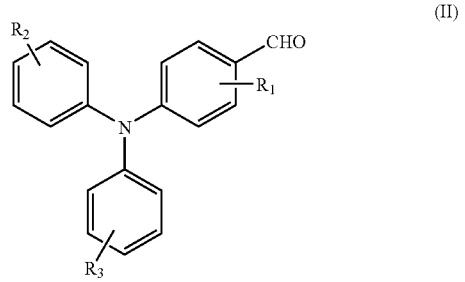

wherein $R_1$, $R_2$, and $R_3$ can be as defined above with respect to formula (I).

The present process can be selected to prepare a monoformylated arylamine which can be used as building blocks for charge transport materials in photoconductive imaging members. For example, the monoformyl arylamine can be used to form a hydrazone. One of ordinary skill in the art would know how to form a hydrazone from a monoformyl arylamine. The hydrazone can be used as a charge-transport material. The charge-transport material can be used in a photoconductive imaging member.

The photoconductive imaging member can comprise a substrate, an optional blocking layer, a photogenerating layer, a charge transport layer, and optionally thereover an overcoat layer that can comprise a polymer with a low dielectric constant and charge transport molecules.

The photogenerating layer can comprise photogenerating pigments dispersed in a resinous binder. The photogenerating pigments can be present in any effective or desired amount, such as from about 5% to about 95% by weight, for example from about 10% to about 80%, and as a further example from about 20% to about 70%. Non-limiting examples of photogenerating layer components include trigonal selenium, titanyl phthalyocyanines, perylenes, hydroxygallium phthalocyanine, metal phthalocyanines, vanadyl phthalocyanines, and metal free phthalocyanines. The resinous binder can be selected from the group consisting of polyesters, polyvinyl butyrals, polycarbonates, polystyrene-b-polyvinyl pyridine, and polyvinyl formals.

The photoconductive imaging members can be selected from a number of different known imaging and printing processes including, for example, color processes, digital imaging process, digital printers, PC printers, and electrophotographic imaging processes, for example xerographic imaging and printing processes wherein charged latent images can be rendered visible with toner compositions of an appropriate charge polarity.

In an embodiment, there is disclosed a method of imaging that can comprise generating an electrostatic latent image on an imaging member, developing the latent image, and transferring the developed electrostatic image to a suitable substrate.

The substrate layer can be opaque or substantially transparent, and can comprise any suitable material having the requisite mechanical properties. Thus, the substrate can comprise a layer of insulating material including inorganic or organic polymeric materials, such as MYLAR® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass or the like. The substrate can be flexible, seamless, or rigid, and can have a number of many different configurations, such as for example a plate, a cylindrical drum, a scroll, an endless flexible belt, and the like. In one embodiment, the substrate can be in the form of a seamless flexible belt. In some situations, it can be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer can be of substantial thickness, for example in excess of about 3,000 microns, or of a minimum thickness. In embodiments, the thickness of this layer can be from about 75 microns to about 300 microns, and more specifically, from about 70 to about 150 microns.

The photogenerating layer can contain known photogenerating pigments, such as metal phthalocyanines, metal free phthalocyanines, hydroxygallium phthalocyanines, perylenes, such as bis(benzimidazo) perylene, titanyl phthalocyanines, and the like, and more specifically, vanadyl phthalocyanines, Type V hydroxygallium phthalocyanines, Type IV titanyl phthalocyanine, and inorganic components, such as selenium, especially trigonal selenium. The photogenerating pigment can be dispersed in a resin binder, or alternatively no resin binder can be needed. Generally, the thickness of the photogenerator layer depends on a number of factors, including the thicknesses of the other layers and the amount of photogenerator material contained in the photogenerating layers. Accordingly, this layer can be of a thickness of, for example, from about 0.05 micron to about 10 microns, and more specifically, from about 0.25 micron to about 3 microns when, for example, the photogenerator compositions are present in an amount of from about 30 to about 75 percent by volume. The maximum thickness of the layer in an embodiment can be dependent primarily upon factors, such as photosensitivity, electrical properties and mechanical considerations. The photogenerating layer binder resin, present in various suitable amounts, for example from about 1 to about 50, and more specifically, from about 1 to about 10 weight percent, can be selected from a number of known polymers, such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. In embodiments of the present disclosure, it can be desirable to select a coating solvent that does not substantially disturb or adversely affect the other previously coated layers of the device. Non-limiting examples of solvents that can be selected for use as coating solvents for the photogenerator layer include ketones, alcohols, aromatic hydrocarbons, halogenated aliphatic hydrocarbons, ethers, amines, amides, esters, and the like. Specific non-limiting examples include cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethyl formamide, dimethyl acetamide, butyl acetate, ethyl acetate, methoxyethyl acetate, and the like.

The coating of the photogenerator layers in embodiments of the present disclosure can be accomplished with spray, dip or wire-bar methods such that the final dry thickness of the photogenerator layer can be, for example, from about 0.01 to about 30 microns, and more specifically, from about 0.1 to about 3 microns after being dried at, for example, about 40° C. to about 150° C. for about 15 to about 90 minutes.

Illustrative examples of polymeric binder materials that can be selected for the photogenerator layer can be as indicated herein, and include those polymers as disclosed in U.S. Pat. No. 3,121,006, the disclosure of which is totally incorporated herein by reference. In general, the effective amount of polymer binder that can be utilized in the photogenerator layer can be from about 0 to about 95 percent by weight, and for example from about 25 to about 60 percent by weight of the photogenerator layer.

As optional adhesives usually in contact with the supporting substrate layer, there can be selected various known substances inclusive of polyesters, polyamides, poly(vinyl butyral), poly(vinyl alcohol), polyurethane and polyacrylonitrile. This layer can be, for example, of a thickness of from about 0.001 micron to about 1 micron. Optionally, this layer can contain effective suitable amounts, for example from about 1 to about 10 weight percent, of conductive and nonconductive particles, such as zinc oxide, titanium dioxide, silicon nitride, carbon black, and the like, to provide, for example, in embodiments of the present disclosure, desirable electrical and optical properties.

Generally, the charge transport layer contains from about 10 to about 75 percent by weight of the charge transport material, and more specifically, from about 35 percent to about 50 percent of this material. The charge transport material can be selected from the group consisting of a hydrazone formed from the disclosed monoformyl arylamine, the disclosed monoformyl arylamine, and mixtures thereof. In an embodiment, the charge transport material can be present in the charge transporting layer, which generally can be of a thickness of from about 5 microns to about 80 microns, and for example can be of a thickness of from about 10 microns to about 44 microns.

Non-limiting examples of the overcoat layer, which layer in embodiments can be of a thickness, for example, of about 0.1 to about 25, more specifically from about 1 to about 10, and yet more specifically from about 1 to about 5 microns, in contact with the charge transport layer or in embodiments the photogenerating layer, include a low dielectric constant (E<2.5) polymer and a charge transport molecule, or charge transport molecule mixtures with a weight ratio of, for example, from about 30/70 to about 80/20, more specifically from about 50/50 to about 75/25, and yet more specifically from about 60/40 to about 75/25. Polymer examples include but are not limited to amorphous poly(phenylene ethers), available from Creanova Inc. as VESTORAN 1900 PPE™ with a glass transition temperature, Tg, of 190° C. and a dielectric constant of 2; poly(cyclo olefins) PCOs available from Zeon Chemical as ZEONOR 1600™, with a Tg of 163° C. and a dielectric constant of 2.27; heat resistant poly (cyclohexylenedimethylene terephthalates) PCTs available from Eastman Chemical as EASTAR AN004™ copolyesters with a temperature of deflection greater than 103° C. and a dielectric constant of 2.1; nylon 12 available from Creanova Inc. as VESTAMIDE L1940™ with a temperature of deflection equal to 110° C. and a dielectric constant equal to 2; fluorinated polymers available from E.I. DuPont Company as 4100 FEP™, a fluorinated ethylene propylene polymer with a melting temperature equal to 259° C. and a dielectric constant equal to 2; polystyrene available from Creanova Inc. as VESTYRON 325™ with a glass transition temperature equal to 89° C. and a dielectric constant equal to 2, and polypropylene available from BASF as NOVOLEN™ with a Viscat softening temperature equal to 92° C. and a dielectric constant equal to 2.3.

Also included within the scope of the present disclosure are methods of imaging and printing with the photoresponsive devices illustrated herein. These methods generally involve the formation of an electrostatic latent image on the imaging member, followed by developing the image with a toner composition comprised, for example, of thermoplastic resin, colorant, such as pigment, charge additive, and surface additives, reference U.S. Pat. Nos. 4,560,635 and 4,338,390, the disclosures of which are totally incorporated herein by reference, subsequently transferring the image to a suitable substrate, and permanently affixing the image thereto. In those environments wherein the device can be used in a printing mode, the imaging method involves the same steps with the exception that the exposure step can be accomplished with a laser device or image bar.

The following examples are set forth as representative of the present process. These examples are not to be construed as limiting the scope of the disclosure as these and other equivalent embodiments will be apparent in view of the present disclosure and accompanying claims.

EXAMPLE 1

Vilsmeier Reaction of Triarylamine in the Presence of Acetonitrile

Vilsmeier Reagent was pre-prepared by adding 30.7 grams (0.2 mol) phosphorus oxychloride dropwise to 14.6 grams (0.2 mol) N,N-dimethylformamide under nitrogen, while submersed in an ice bath. 12.9 grams (0.04 mol) of triarylamine, 122.63 grams (1.24 mol) of 1,2-dichloroethane, 50.87 grams (1.24 mol) of acetonitrile, and 47.3 grams (0.2 mol) of pre-prepared Vilsmeier Reagent were charged into a 500 milliliter reaction flask. The reaction mixture was heated to 80° C. under nitrogen with stirring. The temperature was maintained for 13 hours with samples drawn intermittently. The reaction system was then cooled to room temperature with water gradually added during cooling. The reaction system was then neutralized with sodium bicarbonate and washed several times with water until a neutral pH was obtained. Samples were analyzed by high performance liquid chromatography (HPLC) to determine reaction conversion. Trace levels of triarylamine and bisformylated triarylamine were present in the first sample, which was drawn when the reaction temperature reached 80° C. The HPLC results are set forth in Table 1.

COMPARATIVE EXAMPLE 1A

Vilsmeier Reaction of Triarylamine in the Absence of Acetonitrile

Into a 500 milliliter reaction flask, the following were charged: 52.9 grams (0.16 mol) of triarylamine, 350 grams of 1,2-dichloroethane and 186.4 grams (0.82 mol) of pre-prepared Vilsmeier Reagent as described in Example 1 above. The reaction mixture was heated to 85° C. under nitrogen with stirring. The temperature was maintained for 5 hours with samples drawn intermittently. Samples were analyzed by HPLC to determine reaction conversion. The HPLC results are set forth in Table 1.

COMPARATIVE EXAMPLE 1B

Vilsmeier Reaction of Triarylamine in the Absence of Solvent

Into a 500 ml reaction flask the following were charged: 70.55 grams (0.22 mol) of triarylamine and 80.2 grams (1.1 mol) of N,N-dimethylformamide. 168.3 g (1.1 mol) of phosphorus oxychloride was added drop wise to the reaction mixture under nitrogen and cooling. The reaction mixture was heated to 90° C. under nitrogen with stirring. The temperature was maintained for several hours with samples drawn intermittently. Samples were analyzed by HPLC to determine reaction conversion. The HPLC results are set forth in Table 1.

TABLE 1

|  | Time (h) | % Bisformyl Triarylamine (HPLC) | % Monoformyl Triarylamine (HPLC) | % Triarylamine (HPLC) |
|---|---|---|---|---|
| Example 1 | 0 | 0.4 | 97.9 | 0.2 |
|  | 6 | 0.8 | 98.0 | 0.8 |
|  | 13 | 1.2 | 96.0 | 0.5 |
| Comparative Example 1A | 1 | 2.12 | 97.29 | 0.18 |
|  | 5 | 16.01 | 80.15 | 2.05 |
| Comparative Example 1B | 2 | 20.0 | 80.0 | 0 |
|  | 8 | 53.0 | 41.0 | 0 |

EXAMPLE 2A

Vilsmeier Reaction of Triarylamine with Reduced Vilsmeier Reagent (3.0 Molar Equivalent) in the Presense of Acetonitrile as the Only Solvent Into a 1 Liter reaction flask the following were charged: 48.21 grams (0.15 mole) of triarylamine, 32.89 grams (0.45 mol) of N,N-dimethylformamide and 140 grams acetonitrile. 69 grams (0.45 mol) of phosphorus oxychloride was added drop wise to the reaction mixture under nitrogen and cooling. The reaction mixture was heated to reflux (about 82° C.) under nitrogen and stirring. The temperature was maintained for 1 hour with samples drawn intermittently. The reaction mixture was cooled to room temperature. Deionized water was added and the mixture was allowed to stir overnight. Pale yellow solids were filtered and washed with deionized water until a neutral pH was obtained. The product was dried under vacuum at 50° C. The final product was analyzed by high performance liquid chromatography, differential scanning calorimetry (DSC) and thermogravimetric analysis (TGA). The final yield was calculated by dividing actual mass by expected mass. The results are set forth in Table 2.

EXAMPLE 2B

Vilsmeier Reaction of Triarylamine with Reduced Vilsmeier Reagent (2.5 Molar Equivalent) in the Presence of Acetonitrile as the Only Solvent Into a 1 Liter reaction flask the following were charged: 96.42 grams (0.3 mol) of triarylamine, 54.82 grams (0.75 mol) of N,N-dimethylformamide and 125 g acetonitrile. 115 grams (0.75 mol) of phosphorus oxychloride was added drop wise to the reaction mixture. The reaction mixture was heated to reflux (about 82° C.) under nitrogen and stirring. The temperature was maintained for 1 hour with samples drawn intermittently. The reaction mixture was cooled to room temperature. Deionized water was added and the mixture was allowed to stir overnight. Pale yellow solids were filtered and washed with deionized water until a neutral pH was obtained. The product was dried under vacuum at 50° C. The final product was analyzed by high performance liquid chromatography, differential scanning calorimetry (DSC) and thermogravimetric analysis (TGA). The final yield was calculated by dividing actual mass by expected mass. The results are set forth in Table 2.

EXAMPLE 2C

Vilsmeier Reaction of Triarylamine with Reduced Vilsmeier Reagent (2.1 Molar Equivalent) in the Presence of Acetonitrile as the Only Solvent Into a 1 Liter reaction flask the following were charged: 96.42 grams (0.3 mol) of triarylamine, 46.05 grams (0.63 mol) of N,N-dimethylformamide and 125 grams acetonitrile. 96.6 grams (0.63 mol) of phosphorus oxychloride was added drop wise to the reaction mixture. The final product was analyzed by high performance liquid chromatography, DSC and TGA. The final yield was calculated by dividing actual mass by expected mass. The results are set forth in Table 2.

TABLE 2

|  | Molar Equivalent of Vilsmeier Reagent | % Triarylamine (HPLC) | % Monoformyl Triarylamine (HPLC) | % Bisformyl Triarylamine (HPLC) | DSC melting point (° C.) | TGA volatiles (% wt) | Yield (%) |
| --- | --- | --- | --- | --- | --- | --- | --- |
| Example 2A | 3.0 | 0 | 99.4 | 0.58 | 122.12-125.41 | 1.06 | 96 |
| Example 2B | 2.5 | 0 | 99.4 | 0.58 | 122.93-125.45 | 0.70 | 96 |
| Example 2C | 2.1 | 0.4 | 99.1 | 0.48 | 123.2-124.68 | 1.14 | 97 |

The use of a solvent system has alleviated the safety issues pertaining to mixing of a highly viscous reaction mixture and has provided a heat sink for the potentially exothermic Vilsmeier reagent. The use of acetonitrile has led to a cleaner product without overreaction. The product is easily isolated in high yields and requires no further purification. The process provides high yields that are substantially free of bisformylated reaction product, for example, at least 90% of the substituted or unsubstituted arylamine or a mixture thereof is converted to the monoformyl arylamine and as a further example at least 95% of the substituted or unsubstituted arylamine or a mixture thereof is converted to the monoformyl arylamine.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A process comprising reacting an arylamine with a Vilsmeier reagent and acetonitrile as a sole solvent to form a monoformyl arylamine.

2. The process of claim 1, wherein the arylamine is a substituted arylamine, an unsubstituted arylamine, or a mixture thereof.

3. A process comprising reacting an arylamine with a Vilsmeier reagent and a solvent system comprising acetonitrile as a first solvent and a second solvent selected from an aromatic solvent, an aliphatic solvent, or a combination thereof.

4. The process of claim 3, wherein the second solvent comprises toluene, xylene, chlorobenzene, dichlorobenzene, dichloromethane, 1,2-dichloroethane, or a combination thereof.

5. The process of claim 3, wherein the second solvent comprises 1,2-dichloroethane, toluene, or a combination thereof.

6. The process of claim 1, wherein the reaction is conducted at a temperature of about room temperature to about 90° C.

7. The process of claim 1, wherein the reaction is conducted at a temperature of about 70° C. to about 85° C.

8. The process of claim 1, wherein the reaction is conducted at a temperature of about 80° C. to about 85° C.

9. The process of claim 1, wherein the reaction time is up to about 3 hours.

10. The process of claim 1, wherein the reaction time is less than about 1 hour.

11. The process of claim 1, wherein a monoformyl triarylamine is formed.

12. The process of claim 1, wherein the Vilsmeier reagent is prepared from an N-substituted formamide and a halogenating agent.

13. The process of claim 12, wherein the N-substituted formamide is N,N-dimethylformamide, N-methylformanilide, N-formylmorpholine, and N,N-diisopropylformamide, or a combination thereof; and wherein the halogenating agent is phosphorus oxychloride, pyrophosphoryl chloride, phosgene, oxalyl chloride, thionyl chloride, triphenylphosphine-bromine complex, and hexachlorotriphosphor triene, or a combination thereof.

14. The process of claim 11, wherein the Vilsmeier reagent is selected in an amount comprising about 3 molar equivalents of Vilsmeier reagent to triarylamine.

15. The process of claim 11, wherein the Vilsmeier reagent is selected in an amount comprising about 2 molar equivalents of Vilsmeier reagent to triarylamine.

16. The process of claim 1, wherein the Vilsmeier reagent is selected in an amount comprising about 1.1 molar equivalents of Vilsmeier reagent to triarylamine.

* * * * *